(12) United States Patent
Sims et al.

(10) Patent No.: US 6,887,684 B2
(45) Date of Patent: May 3, 2005

(54) MYD88 ADAPTER-LIKE PROTEINS

(75) Inventors: John E. Sims, Seattle, WA (US);
Timothy A. Bird, Bainbridge Island, WA (US); Luke A. J. O'Neill, Dublin (IE)

(73) Assignee: Immunex Corporation, Seattle, WA (US)

(*) Notice: Subject to any disclaimer, the term of this patent is extended or adjusted under 35 U.S.C. 154(b) by 101 days.

(21) Appl. No.: 09/860,696

(22) Filed: May 17, 2001

(65) Prior Publication Data

US 2002/0164640 A1 Nov. 7, 2002

Related U.S. Application Data

(60) Provisional application No. 60/204,956, filed on May 17, 2000.

(51) Int. Cl.$^7$ .......................... C12P 21/02; C12N 1/19; C12N 15/63; C12N 5/10; C07H 21/04

(52) U.S. Cl. .............. 435/69.1; 435/252.3; 435/254.11; 435/320.1; 435/325; 536/23.5

(58) Field of Search .............................. 435/69.1, 252.3, 435/254.11, 320.1, 325, 7.1; 536/23.5; 530/350

(56) References Cited

U.S. PATENT DOCUMENTS 5,965,421 A * 10/1999 Ni et al. ...................... 435/194

FOREIGN PATENT DOCUMENTS

WO    WO 00/60080    10/2000

OTHER PUBLICATIONS

Hattori et al. The Institute of Physical and Chemical Research RIKEN, Genomic Science Center; 1–7–22 Suehiro–chou, Tsurum ku, Yokohama, Kanagawa 230–0045, Japan; Submitted Mar. 1, 2000.*

Andreakos, E. et al., "Distinct pathways of LPS–induced NF–κB activation and cytokine production in human myeloid and non–myeloid cells defined by selective utilization of MyD88 and Mal/TIRAP," *Blood, Pre-published online* Nov. 20, 2003.

Bannerman, D. et al., "TIRAP mediates endotoxin–induced NF–κB activation and apoptosis in endothelial cells," *Biochem. and Biophys. Res. Commun.*, 295:157–162, 2002.

Bonnert, T. P. et al., "The cloning and characterization of human MyD88: a member of an IL–1 receptor related family," *FEBS Letters*,402(1):81–84, 1997.

Burns, K. et al., "MyD88, an adapter protein involved in interleukin–1 signaling," *J. Biol. Chem.*, 273(20):12203–12209, 1998.

Doyle, S. E. et al., "Toll–like receptor 3 mediates a more potent antiviral response than toll–like receptor 4," *J. Immunol.*, 170:3565–3571, 2003.

Fitzgerald, K. A. et al., "Mal (MyD88–adapter–like) is required for toll–like receptor–4 signal transduction," *Nature*, 413:78–83, 2001.

Flo, T. et al., "Human toll–like receptor 2 mediates monocyte activation by *Listeria monocytogenes*, but not by group B streptococci or lipopolysaccharide," *J. Immunol.*, 164:2064–2069, 2000.

Horng, T. et al., "The adapter molecule TIRAP provides signalling specificity for toll–like receptors," *Nature*, 420:329–333, 2002.

Horng, T. et al., "TIRAP: an adapter molecule in the toll signaling pathway," *Nat. Immunol.*, 2(9):835–841, 2001.

Jovanovic, D. et al., "Stimulation of 92–kd gelatinase (matrix metalloproteinase 9) production by interleukin–17 in human monocyte/macrophages," *Arthritis & Rheumatism*, 43(5):1134–1144, 2000.

Kopp, E. and Medzhitov R., "Recognition of microbial infection by toll–like receptors," *Curr. Opin. Immunol.*, 15:396–401, 2003.

Li, X. et al., "Phosphoinositide 3 kinase mediates toll–like receptor 4–induced activation of NF–κB in endothelial cells," *Infect. Immun.*, 71(8):4414–4420, 2003.

Means, T K. et al., "The biology of toll–like receptors," *Cytokine & Growth Factor Reviews*, 11:219–232, 2000.

Muzio, M. et al., "IRAK (Pelle) family member IRAK–2 and MyD88 as proximal mediators of IL–1 signaling," *Science*, 278:1612–1615, 1997.

Okamura, Y. et al., "The extra domain A of fibronectin activates toll–like receptor 4," *J. Biol. Chem.*, 276(13):10229–10233, 2001.

O'Neill, L. et al., "Mal and MyD88: adapter proteins involved in signal transduction by toll–like receptors" *J Endotoxin Res.*, 9:(1):55–59, 2003.

O'Neill, L., "Toll–like receptor signal transduction and the tailoring of innate immunity: a role for Mal?" *Trends in Immunol.*, 23(6):296–300, 2002.

O'Neill, L., "Signal transduction pathways activated by the IL–1 receptor/toll–like receptor superfamily," *Curr. Top. Microbiol. Immunol.*, 270:47–61, 2002.

O'Neill, L., "The role of MyD88–like adapters in toll–like receptor signal transduction," *Biochem. Soc. Trans.*, 31:643–647, 2003.

Otte, J.M., "Intestinal myofibroblasts in innate immune responses of the intestine," *Gastroenterol.*, 124:1866–1878, 2003.

(Continued)

*Primary Examiner*—Robert A. Wax
(74) *Attorney, Agent, or Firm*—Janis C. Henry

(57) ABSTRACT

There are disclosed MAL-1 polypeptides and active fragments of MAL-1, including fragments that associate with IRAK2. Further disclosed are DNAs encoding the polypeptides and fragments as well as methods of using the DNAs and polypeptides.

9 Claims, No Drawings

OTHER PUBLICATIONS

Schilling, D. et al., "Toll–like receptor 4 and toll–IL–1 receptor domain–containing adapter protein (TIRAP)/myeloid differentiation protein 88 adapter–like (MAL) contribute to maximal IL–6 expression in macrophages," *J. Immunol.*, 169:5874–5880, 2002.

Shinobu, N. et al., "Involvement of TIRAP/MAL in signaling for the activation of interferon regulatory factor 3 by lipopolysaccharide," *FEBS Lett.*517: 251–256, 2002.

Slack, J. et al., "Identification of two majors sites in the type I interleukin–1 receptor cytoplasmic region responsible for coupling to pro–inflammatory signaling pathways," *J. Biol. Chem.*, 275(7):4670–4678, 2000.

Takeda, K. and Akira, S., "Toll receptors and pathogen resistance," *Cell. Microbiol.*, 5(3):143–153, 2003.

Takeda, K. and Akira, S., "TLR signaling pathways," *Semin. Immunol.*, 16:3–9, 2004.

Toshchakov, V. et al., "TLR2 and TLR4 agonists stimulate unique repertoires of host resistance genes in murine macrophages: interferon–β–dependant signaling in TLR4–mediated responses," *J. Endotox. Res.*, 9(3):169–175, 2003.

Toshchakov, V. et al., "TLR4, but not TLR2, mediates IFN–β–induced STAT1 α/β–dependent gene expression in macrophages," *Nature Immunol.*, 3(4):392–398, 2002.

Vogel, S.N. and Fenton, M., "Toll–like receptor 4 signalling: new perspectives on a complex signal–transduction problem," *Biochem. Soc. Trans.*, 31:664–668, 2003.

Wesche, H. et al., "MyD88: an adapter that recruits IRAK to the IL–1 receptor complex," *Immunity*, 7:837–847, 1997.

Yamamoto, M. et al., "Essential role for TIRAP in activation of the signalling cascade shared by TLR2 and TLR4," *Nature*, 420:324–329, 2002.

Yamamoto, M. et al., "TIR domain–containing adaptors define the specificity of TLR signalling," *Mol. Immunol.*, 40:861–868, 2004.

* cited by examiner

MYD88 ADAPTER-LIKE PROTEINS

CROSS REFERENCE TO RELATED APPLICATIONS

This application claims the benefit of U.S. provisional patent application Ser. No. 60/204,956, filed May 17, 2000.

BACKGROUND OF THE INVENTION

1. Field of the Invention

The invention is directed to novel biological compounds. More particularly the present invention relates to MyD88 Adapter-Like-1 (MAL-1) DNA, polypeptides encoded by the DNA, processes for producing the polypeptides, antibodies specific to the polypeptides and uses thereof.

2. Description of Related Art

The Interleukin-1 (IL-1) pathway is a cellular signaling pathway is that plays a crucial role in the mammalian inflammatory response. Several different receptors and ligands are involved in this pathway, including the ligands IL-1 alpha, IL-1 beta and IL-1 receptor antagonist (IL-1ra), and two IL-1 receptors referred to as IL-1 receptor Type I (IL-1RI) and IL-1 receptor Type II (IL-1RII); a soluble form of the latter also exists. Of these, it appears that IL-1LRI is the signaling receptor, whereas IL-1RII does not transduce signal to a cell, but instead may be involved in regulating an IL-1-mediated response (Colotta et al., *Immunol. Today* 15:562; 1994).

Signaling via the IL-1 pathway is complex, requiring a number of accessory molecules in addition to IL-1RI, including a receptor-associated kinase and an adapter molecule. Formation of the receptor complex leads to the activation of Nuclear Factor kappa B (NFkappaB), a transcription factor central to the regulation of an inflammatory response. Toll-like receptors (TLRs) belong to a superfamily of proteins which contain the Toll 1L-1 receptor domain (TIR). The 10 Toll-like receptors in the human genome recognize microbial products during innate immunity and signal through their TIR. A TLR-4 homodimer signals during the immune response to LPS.

MyD88 is an adapter molecule associated with the IL-1R signaling complex that was originally identified in murine myeloleukemic cells. It has areas of homology with both the IL-1R signaling domain and with the so-called death domains found in Tumor Necrosis Receptor (TNFR) family members (Bonnert et al., *FEBS Letters* 402:81; 1997).

Signaling by TLRs also employs MyD88 and induces activation of NF-κB via the kinase IRAK, similar to IL-1R-mediated NF-κB activation. MyD88 is a cytoplasmic TIR domain-containing protein and also contains an N-terminal death domain. Both the death domain and TIR domain of MyD88 recruit the IL-1 receptor associated Kinase (IRAK) and IRAK-2 during signal transduction. Like the TLRs, IL-1R signals through MyD88 and utilizes MyD88 to recruit the kinases IRAK1 and IRAK2.

IL-1 has been implicated in a variety of diseases and conditions, including rheumatoid arthritis, multiple myeloma, osteoporosis, endotoxemia and sepsis, osteoarthritis, inflammatory bowel disease and allergy. Inhibition of the signaling of IL-1 using soluble forms of IL-1Rs, and the IL-1ra, have been shown to be useful in treating or ameliorating disease characterized by excess levels of IL-1 (Bresnihan et al., *Arthritis Rheum.* 41:2196, 1998; Bresnihan et al., *Ann. Rheum. Dis.* 58 Suppl. 1:196, 1999; Bendele et al., *Arthritis Rheum.* 42:498, 1999; van den Berg et al., *Clin. Exp. Rheumatol.* 17 Suppl. 18:S105, 1999; Joosten et al., *J. Immunol.* 163:5049, 1999). Other parts of the IL-1 signaling pathway have also been the target of attempts to identify additional molecules that can be used therapeutically to intervene in conditions related to IL-1. Thus, there is a need in the art to identify novel molecules involved in the IL-1 signaling pathway, both as tools with which to investigate cell signaling and for use in identifying inhibitors of IL-1 signaling.

SUMMARY OF THE INVENTION

The present invention is based upon the identification and isolation of DNA that is similar to MyD88 and other members of the IL-1R/Toll family. The present invention encompasses, in part, MyD88 Adapter Like-1 (MAL-1) DNA and MyD88 Adapter Like-1 (MAL-1) polypeptides encoded by the DNA as shown in SEQ ID NO:1 and SEQ ID NO:2. The invention further provides methods for using the DNA and polypeptides described herein. More particularly, the present invention includes methods of using DNA or DNA fragments as probes or primers to identify DNA encoding proteins having MAL-1 activity and methods for using single-stranded sense or antisense oligonucleotides to inhibit expression and/or function of polynucleotides encoded by the MAL-1 DNA. The present invention further provides methods for identifying inhibitors and enhancers of MAL-1 protein association or MAL-1 function, and, the invention provides methods for using MAL-1 polynucleotides and/or MAL-1 polypeptides to identify other molecules involved in IL-1 signaling. Further, included in the present invention are methods for using MAL-1 polypeptides and polypeptide fragments to generate antibodies, and methods for using the antibodies to purify MAL-1 polypeptides and treat disorders or diseases associated with IL-1 signaling.

In other embodiments, the invention provides a DNA selected from the group consisting of: (a) a DNA encoding a polypeptide comprising about 216 contiguous amino acids of SEQ ID NO:2, from amino acids x1 to x2, wherein x1 represents any of the amino acids in positions 1 through 10 of SEQ ID NO:2, and x2 represents any of the amino acids in positions 226 through 236 of SEQ ID NO:2; (b) a DNA encoding a polypeptide comprising about 135 contiguous amino acids of SEQ ID NO:2, from amino acids x1 to x2, wherein x1 represents any of the amino acids in positions 81 through 91 of SEQ ID NO:2, and x2 represents any of the amino acids in positions 226 through 236 of SEQ ID NO:2; (c) DNA encoding fragments of the polypeptides of (a) or (b), wherein the fragments bind a MAL-1 binding partner; and (d) DNA encoding a polypeptide that is at least 80% identical the polypeptides of (a), (b), or (c), or DNAs capable of hybridization to the DNA of (a) or (b) under conditions of moderate stringency (or high stringency), wherein the DNA encodes a polypeptide of the invention (i.e., a polypeptide that binds a MAL-1 binding partner).

Also included within the scope of the invention are DNAs that encode a fusion protein comprising a MAL-1 polypeptide and a polypeptide, for example, selected from the group consisting of an immunoglobulin Fc domain, a FLAG™ tag, a peptide comprising at least about 6 His residues, a leucine zipper, a GFP peptide, a PkA peptide, a birA peptide, and a GST peptide. Additional useful DNAs are disclosed herein, including an isolated DNA comprising 17 contiguous nucleotides of SEQ ID NO:1, between nucleotide 411 and 569 of SEQ ID NO:1; an isolated DNA comprising 30 contiguous nucleotides of SEQ ID NO:1, between nucleotide 399 and 581 of SEQ ID NO:1; and an isolated DNA comprising 60 contiguous nucleotides of SEQ ID NO: 1, between nucleotide 369 and 611 of SEQ ID NO:1.

In yet another embodiment, the invention provides a polypeptide selected from the group consisting of: (a) a polypeptide comprising about 216 contiguous amino acids of SEQ ID NO:2, from amino acids x1 to x2, wherein x1 represents any of the amino acids in positions 1 through 10 of SEQ ID NO:2, and x2 represents any of the amino acids in positions 226 through 236 of SEQ ID NO:2; (b) a polypeptide comprising about 135 contiguous amino acids of SEQ ID NO:2, from amino acids x1 to x2, wherein x1 represents any of the amino acids in positions 81 through 91 of SEQ ID NO:2, and x2 represents any of the amino acids in positions 226 through 236 of SEQ ID NO:2; (c) fragments of the polypeptides of (a) or (b), wherein the fragments bind a MAL-1 binding partner; and (d) polypeptides that are at least 80% identical to the polypeptides of (a), (b), or (c).

The invention also provides additional novel peptides, including a peptide selected from the group consisting of: (a) a peptide comprising about 10 contiguous amino acids of SEQ ID NO:2, from amino acids 89 to 132 (inclusive); and (b) peptides that are at least 80% identical to the peptides of (a). Additional peptides are within the scope of the instant invention, including an isolated peptide comprising 32 contiguous amino acids of SEQ ID NO:2, between amino acid 56 and amino acid 160 of SEQ ID NO:2; and an isolated peptide comprising 16 contiguous amino acids of SEQ ID NO:2, between amino acid 71 and amino acid 139 of SEQ ID NO:2. DNAs encoding such peptides are also provided herein. The invention further provides antibodies that specifically bind the inventive peptides, including monoclonal antibodies and human antibodies. Assays for identification of small molecules that regulate IL-1 signaling, utilizing an inventive peptide are also provided.

DETAILED DESCRIPTION OF THE INVENTION

DNA encoding a polypeptide that is similar to MyD88 and other members of the IL-1R/Toll family was identified and subsequently isolated from a dendritic cell library as described in Example 1. The described DNA and its encoded polypeptide of the present invention are termed MyD88 Adapter Like-1 (MAL-1) DNA and MyD88 Adapter Like-1 (MAL-1) polypeptides. The DNA has the polynucleotides sequence described in SEQ ID NO:1 and the encoded polypeptide has the amino acid sequence described in SEQ ID NO:2. As described herein, the discovery of the polynucleotides of the invention enables the recombinant manufacture of MAL-1 polypeptides by constructing expression vectors that include the polynucleotides of the invention and constructing host cells that are transfected or transformed with the expression vectors. This discovery further provides for using the polynucleotides or fragments thereof as probes or primers to identify polynucleotides encoding proteins having MAL-1 activity. Further, and in accordance with the present invention, single-stranded sense or antisense oligonucleotides can be constructed and used to inhibit expression and/or function of polynucleotide encoded by the MAL-1 gene. The discovery of MAL-1 polynucleotides, polypeptides, and fragments, thereof, as identified herein, provides polynucleotides, polypeptides or active fragments thereof for identifying inhibitors of MAL-1 protein association or to identify enhancers of MAL-1 function. Additionally, polynucleotides and polypeptides of this invention can be used to identify other molecules involved in IL-1 signaling and MAL-1 polypeptides and fragments thereof are useful for generating antibodies for use as described herein.

The C-terminal portion of MAL-1 exhibits homology to the cytoplasmic domain of members of the IL-1R/Toll family, as well as with the IL-1R/Toll homologous region of MyD88. Of the various members of the IL-1R/Toll family, MAL-1 most resembles MyD88; the overall level of identity between MAL-1 and MyD88 is 26%, while identity in the IL-1R/Toll homologous region is 28%. The IL-1R homologous domain (the TIR domain) includes amino acids 86–235 of SEQ ID NO:2. DNAs of this invention include polynucleotides that encode polypeptides having the sequence of amino acids 86–235 of SEQ ID NO:2.

Like its homologue, MyD88, the MAL-1 polypeptides of this invention are cytoplasmic proteins containing a TIR domain. The N-terminal region of the MAL-1 of this invention is 75 amino acids shorter than MyD88 and lacks the death domain that is present in MyD88. As described in Example 4, MAL-1 of this invention activates NF-κB, Jun N-terminal kinase and extracellular regulated kinases, EK! and EK2. As further described in Example 5, activation of NF-κB by MAL-1 of this invention requires IRAK2 but not IRAK. As described in examples below, this is unlike its homologue, MyD88, which requires IRAK and IRAK2 for signal transduction. Since an isolated TIR domain from the polypeptides of this invention inhibits NF-κB activation by TLR-4 or LPS. The polypeptides described herein act as an adapter for TLR-4. Studies show that signaling by TLR-4 involves the adapter MyD88 and MAL-1 and MAL-1 selectively recruits IRAK-2 to the adapter complex. Further, the polypeptide described herein is required for TLR-4, but not IL-1 signaling.

The polypeptides of the present invention are widely expressed in human tissue. Using a full-length MAL-1 probe, an mRNA species attributed to MAL-1 was detected at high levels in placenta, liver, kidney, skeletal muscle and heart. After prolonged exposure to the probes, this mRNA species was detected at lower levels in other tissues. Identical results were obtained when a probe that included only the TIR domain was used.

Polynucleotides

In a particular embodiment, the present invention relates to certain polynucleotide molecules that are free from contaminating endogenous material. As used herein, DNA or polynucleotides are in the form of a separate fragment or as a component of a larger nucleic acid construct. The polynucleotides of this invention have been derived from DNA or RNA isolated at least once in quantities sufficient for identification using standard biochemical methods (such as those outlined in Sambrook et al., Molecular Cloning: A Laboratory Manual, 2nd ed., Cold Spring Harbor Laboratory, Cold Spring Harbor, N.Y. (1989)). The polynucleotide sequences are provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The polynucleotides of the invention include DNA in both single-stranded and double-stranded form, as well as the corresponding complementary sequences. DNA includes, for example, cDNA, genomic DNA, chemically synthesized DNA, DNA amplified by PCR, and combinations thereof. Genomic DNA may be isolated by conventional techniques, e.g., using the polynucleotides of SEQ ID NO:1, or a suitable fragment thereof, as a probe. The present invention includes DNAs encoding full-length MAL-1 polypeptides as well as polynucleotides encoding fragments of the full-length polynucleotides. Polynucleotide fragments of the invention include those that encode polypeptides having a functional characteristic of the full-length polypeptide. Alternatively, polynucleotide fragments of the invention include those that encode polypeptides that inhibit a functional characteristic of the full-length polypeptide. Exemplary functional characteristics include the ability to act as an adapter for TLR-4, or the ability to act in the TLR-4 signalling cascade, the ability to recruit and IRAK-2, the ability to associate with MyD88 and the ability to activate NF-κB. Exemplary polynucleotide fragments that are active in TLR-4 signalling, are able to associate with and recruit IRAK-2 and are able to associate with MyD88 include the TIR domain, polynucleotides that encode amino acids 68–236 of SEQ ID NO:2, polynucleotides that encode amino acids 86–236 of SEQ ID NO:2, polynucleotides that encode amino acids 86–217 of SEQ ID NO:2, polynucleotides that encode amino acids 68–217 of SEQ ID NO:2, and polynucleotides that encode amino acids 1–68 of SEQ ID NO:2. In another embodiment, polynucleotide fragments of this invention include polynucleotides that encode amino acids x-236 of SEQ ID NO:2 where x is any of amino acids 68–86 of SEQ ID NO:2. In still another embodiment, fragments that have the described activity include polynucleotides that encode amino acids x1–217, where x1 is any of amino acids 68–86 of SEQ ID NO:2.

The polynucleotides of the invention are preferentially derived from human sources, but the invention includes those derived from non-human species, as well.

The nucleotide sequence of a preferred MAL-1 DNA of the invention is shown in SEQ ID NO:1. A particularly preferred nucleotide sequence includes nucleotides 162–866 of SEQ ID NO: 1. The polypeptide encoded by the DNA of SEQ ID NO:1 has the sequence of amino acids shown in SEQ ID NO:2. Because DNA sequences may be truncated and/or cleaved at any of a number of terminal nucleotides and encode functional polypeptides, the present invention provides DNAs encoding polypeptides having the amino acid sequence x1 to x2 of SEQ ID NO:2, wherein x1 represents any of the amino acids in positions 1 through 10 of SEQ ID NO:2, and x2 represents any of the amino acids in positions 226 through 236 of SEQ ID NO:2. Preferably the truncated or cleaved nucleotides or amino acid residues are other than those defining the IL-1R homologous domain.

Due to the degeneracy of the genetic code, wherein more than one codon can encode the same amino acid, a DNA can vary from those DNA described above and those shown in SEQ ID NO:1, and still encode a polypeptide having the amino acid sequence of SEQ ID NO:2. Such variant DNAs can result from silent mutations that occur naturally, or during PCR amplification, or they can be the product of deliberate mutagenesis of a native sequence.

The invention thus provides isolated DNAs that include (a) DNA having the nucleotide sequence of SEQ ID NO:1 and the above described fragments; (b) DNA encoding the polypeptide of SEQ ID NO:2 and the above described fragments; (c) DNA that is the complement of DNA that is capable of hybridizing to the DNA of (a) or (b) under conditions of moderate stringency and which encodes a polypeptide of the invention; (d) DNA that is the complement of DNA that is capable of hybridizing to the DNA of (a) or (b) under conditions of high stringency and which encodes a polypeptide of the invention, and (e) DNA which is degenerate as a result of the genetic code to a DNA defined in (a), (b), (c), or (d) and which encode polypeptides of the invention.

The basic parameters affecting the choice of hybridization conditions and guidance for devising suitable conditions are set forth by Sambrook et al., 1989. As used herein, conditions of moderate stringency can be readily determined by those having ordinary skill in the art based on, for example, the length and/or base composition of the DNA. For hybridizing probes longer than about 100 nucleotides with filter-bound target DNA or RNA, one way of achieving moderately stringent conditions involves the use of a prewashing solution containing 5XSSC, 0.5% SDS, 1.0 mM EDTA (pH 8.0), hybridization buffer of about 50% formamide, 6XSSC, and a hybridization temperature of about 42øC (or other similar hybridization solutions, such as one containing about 50% formamide, with a hybridization temperature of about 42øC), and washing conditions of about 60øC, in 0.5XSSC, 0.1% SDS.

Conditions of high stringency can also be readily determined by the skilled artisan based on, for example, the length and base composition of the DNA. Generally, such conditions are defined as hybridization conditions as above, but with washing at approximately 68øC, 0.2XSSC, 0.1% SDS. It is understood that the wash temperature and wash salt concentration can be adjusted as necessary to achieve a desired degree of stringency by applying the basic principles that govern hybridization reactions and duplex stability, as known to those skilled in the art (see, e.g., Sambrook et al., 1989). It should be further understood that hybridization conditions for oligonucleotide probes of defined length and sequence can be designed by applying formulae known in the art (e.g., see Sambrook et al., 1989, at 11.4511.47).

The present invention encompasses DNA that encodes fragments of SEQ ID NO:2 that have at least one activity of MAL-1, and DNA encoding polypeptides of at least about 16 amino acids, or of at least about 32 amino acids, which polypeptides are useful as immunogens. DNAs encoding polypeptides comprising inactivated N-glycosylation site(s), inactivated protease processing site(s), or conservative amino acid substitution(s), are also included, as described below. One such fragment is the IL-1R-homologous domain which is useful as a dominant negative regulator of IL-1R signaling, or in an assay to identify small molecules that can inhibit or otherwise regulate IL-1 signaling. Exemplary MAL-1 activities include a role in the TLR-4 signal cascade, the ability to act as an adapter for TLR-4, the ability to recruit and associate with IRAK2 and the ability to interact with MyD88.

In another embodiment, the polynucleotides of the invention also include nucleotide sequences that are at least 80% identical to a native sequence, such as the sequence shown in SEQ ID NO:1, and nucleic acid molecules that are at least 85% identical to a native sequence, such as the sequence shown in SEQ ID NO: 1. Also contemplated are embodiments in which a nucleic acid molecule comprises a sequence that is at least 90% identical, at least 95% identical, at least 98% identical, at least 99% identical, or at least 99.9% identical to a native sequence.

Percent identity is defined as the number of aligned symbols, i.e. nucleotides or amino acids, which are identical, divided by the total number of symbols in the shorter of the two sequences. The degree of homology (percent identity) between two sequences may be determined by using the alignment method of Needleman and Wunsch (*J. Mol. Biol.* 48:443, 1970) as revised by Smith and Waterman (*Adv. Appl. Math* 2:482, 1981), with a unary comparison matrix (containing a value of 1 for identities and 0 for nonidentities) for nucleotides, and the weighted comparison matrix of Gribskov and Burgess (*Nucl. Acids. Res.* 14:6745, 1986) as described by Schwartz and Dayhoff (Atlas of Protein Sequence and Structure, National Biomedical Research Foundation, pp. 353–358, 1979) for amino acids.

Preferably, the comparison is done using a computer program. An exemplary, preferred computer program is the Genetics Computer Group (GCG; Madison, Wis.) Wisconsin package version 10.0 program, 'GAP.' The preferred default parameters for the 'GAP' program includes: (1) The GCG implementation of the previously stated comparison matrixes for nucleotides and amino acids; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by one skilled in the art of sequence comparison may also be used.

Similarly, the DNAs of the invention include variants that differ from a native DNA sequence because of one or more deletions, insertions or substitutions, but that encode a biologically active polypeptide. In addition, DNAs that encode various additions or substitutions of amino acid residues or sequences, or deletions of terminal or internal residues or sequences are encompassed by the invention.

A exemplary MAL-1 variant of the present invention is a polynucleotide that encodes the polypeptide of SEQ ID NO:2 with the proviso that the Pro at amino acid 125 is His. This MAL-1 variant of the present invention does not signal through TLR-4 and thus blocks signalling and is useful for screening for additional receptors that signal TLR-4.

Examples of additional variant DNAs include those that have been modified to facilitate expression of a polypeptide with an altered N-linked glycosylation site or KEX-2 protease site, as well as those in which codons that encode Cys residues that are not necessary for biological activity are eliminated or altered to encode another amino acid. These and other variant peptides are disclosed herein; DNAs encoding them are also encompassed by the invention.

The invention also provides isolated nucleic acids useful in the production of polypeptides. Such polypeptides may be prepared by any of a number of conventional techniques. A DNA sequence encoding a MAL-1 polypeptide, or desired fragment including truncated forms described herein and IL-1R homologous domains may be subcloned into an expression vector for production of the polypeptide or fragment. The DNA sequence advantageously is fused to a sequence encoding a suitable leader or signal peptide.

The desired DNA fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA encoding a desired protein or fragment thereof. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., Science 239:487 (1988); Recombinant DNA Methodology, Wu et al., eds., Academic Press, Inc., San Diego (1989), pp. 189–196; and PCR Protocols: A Guide to Methods and Applications, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The polypeptides of the invention include full length proteins encoded by the polynucleotides set forth above. In one embodiment the present invention provides the polypeptide of SEQ ID NO:2. The present invention further provides polypeptide fragments that retain at least one of the above disclosed activities associated with the MAL-1 polypeptide. One such fragment is the polypeptide having the sequence of amino acids 86 to 236 of SEQ ID NO:2. Other fragments that are active in the TLR-4 signalling cascade or are capable of associating with IRAK2 and/or MyD88 include the polypeptides having the sequence of amino acids 68–236 of SEQ ID NO:2, amino acids 86–236 of SEQ ID NO:2, amino acids 86–217 of SEQ ID NO:2, and amino acids 68–217 of SEQ ID NO:2. Further within the present invention is a polypeptide having amino acids 1–68 of SEQ ID NO:2. In another embodiment, this invention includes polypeptides having the sequence of amino acids x–236 of SEQ ID NO:2 where x is any of amino acids 68–86 of SEQ ID NO:2. In still another embodiment, fragments that have the described activity include polypeptides having the sequence of amino acids x1–217 of SEQ ID NO:2, where x1 is any of amino acids 68–86 of SEQ ID NO:2.

The polypeptide of SEQ ID NO:2 is similar to MyD88 and other members of the IL-1R/Toll family of proteins, especially in the C-terminal 150 amino acids (amino acid 86 to 236 of SEQ ID NO:2). MAL-1 or a fragment thereof may be recombinantly expressed as a soluble polypeptide capable of being secreted from the cells in which it is expressed. Such soluble peptides may be obtained by separating intact cells that express the soluble polypeptide from the culture medium (e.g., by centrifugation or filtration), and isolating the soluble peptide from the medium (supernatant). Purification of the polypeptides from recombinant host cells is facilitated by expression of the polypeptide as a secreted protein, which can be useful in obtaining large amounts of the soluble polypeptide as a therapeutic or diagnostic agent, or for use in assays.

The inventive polypeptides thus include, but are not limited to, polypeptides comprising amino acids x1 to x2 of SEQ ID NO:2, wherein x1 represents any of the amino acids in positions 1 through 10 of SEQ ID NO:2, and x2 represents any of the amino acids in positions 226 through 236 of SEQ ID NO:2. Other embodiments include polypeptides comprising amino acids x1 to x2 of SEQ ID NO:2, wherein x1 represents any of the amino acids in positions 81 through 91 of SEQ ID NO:2, and x2 represents any of the amino acids in positions 226 through 236 of SEQ ID NO:2.

The invention also provides MAL-1 polypeptides and fragments thereof that retain a desired activity. Particular embodiments are directed to polypeptide fragments that retain the ability to bind an MAL-1 binding partner, the ability to act as an adapter for TLR-4, and the ability to recruit or associate with IRAK-2. Other activities associated with polypeptide fragments of the present invention include the ability to inhibit TLR-4 adapter function and inhibit IRAK-2 recruitment. Such a fragment may be a soluble polypeptide, as described above. In another embodiment, the polypeptides and fragments advantageously include regions that are conserved in the MyD88 family as described above.

Also provided herein are polypeptide fragments comprising at least 8, 12, 16, or at least 32, contiguous amino acids of the sequence of SEQ ID NO:2. Such polypeptide fragments may be employed as immunogens in generating antibodies, as small molecule agonists or antagonists of MAL-1 activity, and in various assays for MAL-1.

Naturally occurring variants as well as derived variants of the polypeptides and fragments are provided herein. Variants may exhibit amino acid sequences that are at least 80% identical, or at least about 85% identical, to the native polypeptide disclosed herein. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined as described previously under POLYNUCLEOTIDES.

The variants of the invention include, for example, those that result from alternate MRNA splicing events or from proteolytic cleavage. Alternate splicing of mRNA may, for example, yield a truncated but biologically active protein, such as a naturally occurring, shortened form of the protein. Variations attributable to proteolysis include, for example, differences in the N- or C-termini upon expression in different types of host cells, due to proteolytic removal of one or more terminal amino acids from the protein (generally from about one to about five terminal amino acids) or other differences in protein expression. Proteins in which differences in amino acid sequence are attributable to genetic polymorphism (allelic variation among individuals producing the protein) are also contemplated herein.

One polypeptide variant of the present invention is the polypeptide of SEQ ID NO:2 with the proviso that the Pro at amino acid 125 is His. This polypeptide does not signal through TLR-4 and is useful in screening experiments to determine receptors that signal through TLR-4.

Other variants include fusion proteins, such as those prepared by expression in recombinant culture as N-terminal or C-terminal fusions. Examples of fusion proteins include fusion proteins that will form oligomers, such as a MAL-1/Fc fusion protein (for example, as described in U.S. Pat. No. 5,962,406, issued Oct. 5, 1999), or a zipper fusion protein (U.S. Pat. No. 5,716,805, issued Feb. 10, 1998). Further, fusion proteins can comprise peptides added to facilitate purification and identification (often referred to as tag proteins). Such peptides include, for example, poly-His or the antigenic identification peptides described in U.S. Pat. No. 5,011,912 and in Hopp et al., Bio/Technology 6:1204, 1988. Additional, useful tag proteins include green fluorescent protein (GFP; Chalfie et al., Science 263:802, 1994), an N-terminal peptide that contains recognition sites for a monoclonal antibody, a specific endopeptidase, and a site-specific protein kinase (PKA; Blanar and Rutter, Science 256:1014, 1992), birA (Altman et al., Science 274:94, 1996) .and glutathione S transferase (GST: Smith and Johnson, Gene 67:31, 1988).

One such tag peptide is the FLAG™ peptide, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG™ peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG™ peptide are available from Eastman Kodak Co., Scientific Imaging Systems Division, New Haven, Conn.

Another useful tag peptide is the GST peptide, which binds glutathione, also facilitating purification of expressed recombinant protein. Recombinant protein can be purified by affinity chromatography using a suitable chromatography matrix to which has been attached glutathione, as described in Smith and Johnson, supra, hereby incorporated by reference. Suitable chromatography matrixes include Glutathione-Agarose beads (Pharmacia, Uppsala, Sweden). Recombinant protein can be eluted with an excess of glutathione. Alternatively, a specific enzymatic cleavage site (such as a thrombin cleavage site) can be included n the recombinant fusion protein, and the desired polypeptide removed from the affinity matrix by treatment with the enzyme that cleaves the fusion protein at the cleavage site.

Among the variant polypeptides provided herein are variants of native polypeptides that retain the native biological activity or the substantial equivalent thereof. One example is a variant that binds a binding partner with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such physiochemically conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other substitutions, e.g., involving substitutions of entire regions having similar hydrophobicity characteristics, are well known.

The invention further includes polypeptides of the invention with or without associated native-pattern glycosylation. Polypeptides expressed in yeast or mammalian expression systems (e.g., CHO or COS-7 cells) can be similar to or significantly different from a native polypeptide in molecular weight and glycosylation pattern, depending upon the choice of expression system. Further, a given preparation may include multiple differentially glycosylated species of the protein.

Expression of polypeptides of the invention in bacterial expression systems, such as E. coli, provides non-glycosylated molecules. Glycosyl groups can also be removed through conventional chemical or enzymatic methods, in particular those utilizing glycopeptidase. In general, glycosylated polypeptides of the invention can be incubated with a molar excess of glycopeptidase (Boehringer Mannheim).

Recombinant technology can also be applied to reduce glycosylation that occurs in eukaryotic expression systems, for example, as described in U.S. Pat. No. 5,071,972 and EP 276,846, hereby incorporated by reference. Other variants are prepared by modification of adjacent dibasic amino acid residues, to enhance expression in yeast systems in which KEX2 protease activity is present, as disclosed in EP 212, 914. In another example of variants, sequences encoding Cys residues that are not essential for biological activity can be altered to cause the Cys residues to be deleted or replaced with other amino acids, as disclosed in U.S. Pat. No. 5,962,406, issued Oct. 5. 1999.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Production of Polypeptides and Fragments Thereof

The present invention encompasses expression vectors that contain DNA described herein and host cells containing the expression vectors. Further, the present invention includes methods for preparing polypeptides and polypeptide fragments encoded by the DNA of the present invention using expression vectors and host cells described herein. A method for producing polypeptides comprises culturing the host cells of the present invention transformed with an expression vector that encodes the polypeptide, under conditions that promote expression of the polypeptide. Optionally, the polypeptide is recovered from the culture. The skilled artisan will recognize that procedures for producing and purifying the expressed polypeptides will vary according to such factors as the type of host cells employed, and whether the polypeptide is membrane-bound or a soluble polypeptide that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an niRNA ribosomal binding site, and appropriate sequences which control transcription and translation initiation and termination. An origin of replication that confers the ability to replicate in the desired host cells, and a selection gene by which transformants are identified, are generally incorporated into the expression vector. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the MRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. Accordingly, a protein preparation may include a mixture of protein molecules having different N-terminal amino acids, resulting from cleavage of the signal peptide at more than one site.

Suitable host cells for expressing polypeptides include prokaryotes, yeast or higher eukaryotic cells. Appropriate cloning and expression vectors for use with bacterial, fungal, yeast, and mammalian cellular hosts are described, for example, in Pouwels et al. Cloning Vectors: A Laboratory Manual, Elsevier, N.Y., (1985). Cell-free translation systems could also be employed to produce polypeptides using RNAs derived from DNA constructs disclosed herein.

Mammalian or insect host cell culture systems also may be employed to express recombinant polypeptides. Bacculovirus systems for production of heterologous proteins in insect cells are reviewed by Luckow and Summers, Bio/Technology 6:47 (1988). Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10:2821, 1991).

A commonly used cell line is dihydrofolate reductase (DHFR)-CHO cells which are auxotrophic for glycine, thymidine and hypoxanthine, and can be transformed to the DHFR+phenotype using DHFR cDNA as an amplifiable dominant marker. One such DHFR-CHO cell line, DXB11, was described by Urlaub and Chasin (Proc. Natl. Acad. Sci. USA 77:4216, 1980). Another exemplary DHFR-CHO cell line is DG44 (see, for example, Kaufman, R. J., Meth. Enzymology 185:537 (1988). Other cell lines developed for specific selection or amplification schemes will also be useful with the invention.

Several transfection protocols are known in the art, and are reviewed in Kaufman, R. J., supra. The transfection protocol chosen will depend on the host cell type and the nature of the gene of interest, and can be chosen based upon routine experimentation. The basic requirements of any such protocol are first to introduce DNA encoding the protein of interest into a suitable host cell, and then to identify and isolate host cells which have incorporated the heterologous DNA in a stable, expressible manner. Other useful transfection protocols are discussed in U.S. Pat. No. 6,027,915, issued Feb. 22, 2000.

Transfection of cells with heterologous DNA and selection for cells that have taken up the heterologous DNA and express the selectable marker results in a pool of transfected cells. Individual cells in these pools will vary in the amount of DNA incorporated and in the chromosomal location of the transfected DNA. To generate stable cell lines, individual cells can be isolated from the pools and cultured (a process referred to as cloning).

A method of amplifying the gene of interest is also desirable for expression of the recombinant protein, and typically involves the use of a selection marker (reviewed in Kaufman, R. J., supra). Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for). Several amplifiable markers are suitable for use in the inventive expression vectors (for example, as described in Maniatis, Molecular Biology: A Laboratory Manual, Cold Spring Harbor Laboratory, NY, 1989; pgs 16.9–16.14).

Useful selectable markers for gene amplification in drug-resistant mammalian cells are shown in Table 1 of Kaufman, R. J., supra (1988), and include DHFR-MTX resistance, P-glycoprotein and multiple drug resistance (MDR)-various lipophilic cytoxic agents (i.e., adriamycin, colchicine, vincristine), and adenosine deaminase (ADA)-Xyl-A or adenosine and 2'-deoxycoformycin. Other dominant selectable markers are discussed in U.S. Pat. No. 6,027,915, issued Feb. 22, 2000.

Useful regulatory elements, described previously, can also be included in the plasmids or expression vectors used to transfect mammalian cells. The transfection protocol chosen, and the elements selected for use therein, will depend on the type of host cell used. Those of skill in the art are aware of numerous different protocols and host cells, and can select an appropriate system for expression of a desired protein, based on the requirements of their selected cell culture system(s).

A useful high expression vector, pCAVNOT, has been described by Mosley et al., Cell 59:335–348, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG and pDC311, can also be used. FLAG™ technology is centered on the fusion of a low molecular weight (1 kD), hydrophilic, FLAG™ marker peptide to the N-terminus of a recombinant protein expressed by pFLAG expression vectors. pDC311 is another specialized vector used for expressing proteins in CHO cells. pDC311 is characterized by a bicistronic sequence containing the gene of interest and a dihydrofolate reductase (DBFR) gene with an internal ribosome binding site for DHFR translation, an expression augmenting sequence element (EASE), the human CMV promoter, a tripartite leader sequence, and a polyadenylation site.

A signal peptide may be employed to facilitate secretion of the protein, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367, 566; the type I interleukin-1 receptor signal peptide described in U.S. Pat. No. 4,968,607; and the type II interleukin-1 receptor signal peptide described in EP 460, 846.

MAL-1, in its native form, is an intracellular protein lacking a signal peptide. Recombinant forms of MAL-1 can also be expressed as intracellular proteins that can be isolated from cell lysates, as disclosed herein.

Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other cellular components, such as unrelated proteins or polypeptides, lipids and DNA or RNA, for example, as a purification product of recombinant expression systems such as those described above or as a purified product from a non-recombinant source such as naturally occurring cells and/or tissues.

In one embodiment, the purification of recombinant polypeptides or fragments can be accomplished by expressing the inventive polypeptide(s) as a fusion protein with a peptide (often referred to as a tag peptide) for which an affinity purification scheme is known in the art. Such fusion partners can include the poly-His or other tag peptides described above as well as an Fc moiety or a zipper moiety.

With respect to purification, as is known to the skilled artisan, procedures for purifying a recombinant polypeptide or fragment will vary according to such factors as the type of host cells employed and whether or not the recombinant polypeptide or fragment is secreted into the culture medium. In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps.

As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification.

Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns.

Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. In this aspect of the invention, binding proteins, such as antibodies against MAL-1, or other proteins that bind MAL-1, can be bound to a solid phase support such as a column chromatography matrix or a similar substrate suitable for identifying, separating, or purifying MAL-1. Adherence of MAL-1 to a solid phase contacting surface can be accomplished by any means, for example, magnetic microspheres can be coated with MAL-1-binding proteins and held in the incubation vessel through a magnetic field.

Solutions containing MAL-1 polypeptides are contacted with the solid phase under conditions promoting binding of MAL-1 polypeptides to the binding protein; unbound material is then washed away. Methods of releasing positively selected peptides from the solid phase are known in the art and encompass, for example, use of a high salt elution buffer followed by dialysis into a lower salt buffer, or by changing pH (or other characteristics depending on the affinity matrix utilized), or competitive removal using a naturally occurring substrate of the affinity moiety. The methods are preferably non-injurious to the MAL-1 polypeptides.

In one exemplary method, solutions containing MAL-1 polypeptides of the invention first can be incubated with a biotinylated MAL-1 binding protein. Incubation periods are typically at least one hour in duration to ensure sufficient binding to polypeptides of the invention. The resulting mixture then is passed through a column packed with avidin-coated beads, whereby the high affinity of biotin for avidin provides the binding of the MAL-1 polypeptides to the beads. Use of avidin-coated beads is known in the art. See Berenson, et al. J. Cell. Biochem., 10D:239 (1986). Washing of unbound material and the release of the bound cells are performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like.

Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Uses of MAL-1 Polynucleotides or Oligonucleotides

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO: 1 from other mammalian species are contemplated herein, probes based on the human DNA sequence of SEQ ID NO:1 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Once the chromosome location of the MAL-1 gene is determined the information can be used to identify the chromosome to which it maps. The location of the MAL-1 gene has been determined and placement results from the genebridge 4 mapping are as follows: Chromosome Chr11; Places 1.82 cR from WI-3939; places 4.71 cR from WI-7841 (lod 2.42 relative to most likely); places 0.10 cR from D11S1351 (lod 2.82 relative to most likely). Using The Genome Database website (linked through the ncbi) and searching via the STS markers adjacent to MAL-1, the region this locus corresponds to is 11q23–11 q24.

The polynucleotide of SEQ ID NO:1 or oligonucleotide fragments thereof can be used by those skilled in the art using well-known techniques to identify the human chromosome 11 as well as the specific locus thereof, that contains the DNA of MAL-1 and MAL-1 homologs or family members. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization with PCR techniques using the Whitehead Institute/MIT Center for Genome Research Genebndge4 panel of 93 radiation hybrids See the Whitehead Istitute/MIT Center for Genome Research web site). This technique involves using primers that lie within a putative exon of the gene of interest and which amplify a product from human genomic DNA, but do not amplify hamster genomic DNA. The results of the PCR reactions are converted into a data vector that is submitted to the Whitehead/MIT Radiation Mapping site on the internet. The data is scored and the chromosomal assignment and placement relative to known Sequence Tag Site (STS) markers on the radiation hybrid map is provided. (See the Whitehead Institute/MIT Center for Genome Research web site).

Human chromosome 11, to which the MAL-1 gene maps, is associated with specific diseases which include but are not limited to acute promyelocytic leukemia, porphyria, and thiamine-responsive megaloblastic anemia syndrome. Thus, the polynucleotide or oligonucleotide fragments of SEQ ID NOs:1 can be used to analyze abnormalities associated with genes mapping to loci on chromosome 11. This enables one to distinguish conditions in which this marker is rearranged or deleted.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA of SEQ ID NO: 1. Such a fragment generally comprises at least about 17 nucleotides, preferably from about 17 to about 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of complexes that block or inhibit protein expression by one of several means, as discussed in U.S. Pat. No. 5,783,665, issued Jul. 21, 1998. Organic moieties and other moieties that increases affinity of the oligonucleotide for a target nucleic acid sequence, or intercalating agents, may be attached to sense or antisense oligonucleotides to modify binding specificities of the antisense or sense oligonucleotide for the target nucleotide sequence.

The antisense or sense oligonucleotides may be introduced into a cell containing the target nucleic acid sequence by any gene transfer method, including, for example, lipofection, CaPO4-mediated DNA transfection, electroporation, or by using gene transfer vectors such as Epstein-Barr virus. Sense or antisense oligonucleotides also may be introduced into a cell containing the target nucleotide sequence by formation of a conjugate with a ligand binding molecule, as described in WO 91/04753. Alternatively, a sense or an antisense oligonucleotide may be introduced into a cell containing the target nucleic acid sequence by formation of an oligonucleotide-lipid complex, as described in WO 90/10448.

The inventive DNAs will also be useful in the development of transgenic and/or knockout cells and animals. Those of ordinary skill in the art are aware of various methods by which such cells or animals can be prepared; an exemplary method is given in U.S. Pat. No. 5,565,321, issued Oct. 15, 1996. The techniques described therein can be used with the inventive sequences by the application of routine experimentation.

Uses of MAL-1 Polypeptides

Because MAL-1 is a homolog of MyD88, an important molecule in the signaling cascade for the IL-1R/Toll family of receptors, small molecule inhibitors of its function or its protein associations (or antisense or other inhibitors of its synthesis) will be useful in treating autoimmune and/or inflammatory disorders. Accordingly, the MAL-1 polypeptides and the foregoing described fragments of the present invention are useful in screening assays to identify compounds and small molecules which inhibit (antagonize) or enhance (agonize) the above described functions and activities of the MAL-1 polypeptides.

Thus, for example, polypeptides, and particularly polypeptide fragments of the invention may be used to identify antagonists and agonists from cells, cell-free preparations, chemical libraries, and natural product mixtures. The antagonists and agonists may be natural or modified substrates, ligands, enzymes, receptors, etc. of the polypeptides of the instant invention, or may be structural or functional mimetics of the polypeptides. Potential antagonists of the instant invention may include small molecules, peptides and antibodies that bind to and occupy a binding site of the inventive polypeptides or a binding partner thereof, causing them to be unavailable to bind to their natural binding partners and therefore preventing normal biological activity. Potential agonists include small molecules, peptides and antibodies which bind to the instant polypeptides or binding partners thereof, and elicit the same or enhanced biologic effects as those caused by the binding of the polypeptides of the instant invention.

Small molecule agonists and antagonists are usually less than 10K molecular weight and may possess a number of physicochemical and pharmacological properties which enhance cell penetration, resist degradation and prolong their phsiological half-lives (Gibbs, J., Pharmaceutical Research in Molecular Oncology, Cell, Vol. 79 (1994)).

Antibodies, which include intact molecules as well as fragments such as Fab and F(ab')2 fragments, as well as recombinant molecules derived therefrom, may be used to bind to and inhibit the polypeptides of the instant invention by blocking the propagation of a signaling cascade. It is preferable that the antibodies are humanized, and more preferable that the antibodies are human. The antibodies of the present invention may be prepared by any of a variety of well-known methods.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked irnmunosorbant assays (ELISA) or radioimmunoassays.

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions and the inhibition thereof by small organic molecules, including protein-protein, receptor-ligand, enzyme-substrate, and so on. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for screening test compounds in order to identify small molecule drug candidates, antibodies, peptides, and other antagonists and/or agonists, natural or synthetic.

Thus, a method of the present invention includes screening a test compound to identify its ability to affect the association of polypeptide of this invention with IRAK2. Such a method involves forming a composition that includes IRAK2, a polypeptide of this invention and a test compound, and then assaying for the level of interaction of the polypeptide and IRAK2. If the level of interaction differs from that level of interaction that is observed in the absence of test compound, a test compound that affects the interaction of the polypeptide and IRAK2 is identified. Polypeptides that are useful in the screening methods include the polypeptide of SEQ ID NO:2 and fragments of SEQ ID NO:2 that associate with IRAK as described above.

Another method of the present invention includes screening a test compound to identify its ability to affect the TLR-4 adapter activity of polypeptide of this invention. Such a method involves forming a composition that includes a polypeptide of this invention, TLR-4, and a test compound, and then assaying for a TLR-4 signalling activity, such as NF-κB activity. If the level of signalling activity differs from that level of activity that is observed in the absence of test compound, a test compound that affects the TLR-4 adapter activity of the polypeptide is identified. Polypeptides that are useful in the screening method include the polypeptide of SEQ ID NO:2 and fragments of the polypeptide of SEQ ID NO:2 that maintain activity as a TLR-4 adapter as described above.

Additional screening methods of the present invention include screening a test compound to identify its ability to affect the association of polypeptide of this invention with MyD88. Such a method involves forming a composition that includes MyD88 a polypeptide of this invention and a test compound, and then assaying for the level of interaction of the polypeptide and MyD88. If the level of interaction differs from that level of interaction that is observed in the absence of test compound, a test compound that affects the interaction of the polypeptide and MyD88 is identified. Polypeptide that are useful in the screening method include the polypeptide of SEQ ID NO:2 and fragments of the polypeptide of SEQ ID NO:2 that associate with MyD88 as described above.

The assays described in Examples 4–9 are generally suitable or adaptable for screening test compounds. Screening assays additionally include the presence of a test compound or the absence of a test compound. A difference in the interaction or signaling effect in the presence of the test compound when compared to the absence of a test compound indicates that the test compound is an agonist or antagonist of the interaction or signaling cascade.

In one embodiment of a method for identifying molecules which inhibit or antagonize the MAL-1 polypeptides involves adding a test compound to a medium which contains cells that express the polypeptides of the instant invention; changing the conditions of said medium so that, but for the presence of the test compound, the polypeptides would be bound to their natural ligands, substrates or effector molecules, and observing the binding and stimulation or inhibition of a functional response. The activity of the cells which were contacted with the test compound may then be compared with the identical cells which were not contacted and antagonists and agonists of the polypeptides of the instant invention may be identified. The measurement of biological activity may be performed by a number of well-known methods such as measuring the amount of protein present (e.g. an ELISA) or of the proteins activity. A decrease in biological stimulation or activation would indicate an antagonist. An increase would indicate an agonist.

Screening assays can further be designed to find molecules that mimic the biological activity of the polypeptides of the instant invention. Molecules which mimic the biological activity of a polypeptide may be useful for enhancing the biological activity of the peptide. To identify compounds for therapeutically active agents that mimic the biological activity of a polypeptide, it must first be determined whether a candidate molecule binds to the polypeptide. A binding candidate molecule is then added to a biological assay to determine its biological effects. The biological effects of the candidate molecule are then compared to those of the polypeptide(s).

Another embodiment of the invention relates to uses of MAL-1 to study cell signal transduction. Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Accordingly, these novel MAL-1 polypeptides can be used as reagents to identify novel molecules involved in signal transduction pathways.

The inventive polypeptides are involved in TLR-4 signaling, and as such inhibitors of MAL-1 can be used as inhibitors of the TLR-4 signaling pathway. Accordingly, they find utility in in vitro screening assays and in vivo therapeutics. As therapeutics that are cell membrane permeable, the MAL-1 and fragments of the IL-1R/Toll homologous domain that are necessary for TLR-4 signaling can be administered to agonize or antagonize the signaling pathways, thus providing useful immunoregulators. Various liposome-based compositions of the inventive polypeptides are envisioned herein.

Inhibitors and enhancers of MAL-1 and the polypeptide fragments described herein are useful in treating a variety of medical conditions. MAL-1 signaling and activities are associated with a response to bacterial invasion, inflammation, inducement of dendritic cell maturation, IL-18 expression, cell disorders including cancer, and immune response. Thus, antagonists of MAL-1 activities are useful in treating certain types of immune system dysfunction, autoimmune diseases, inflammatory conditions, complications that are associated with bacterial infections that occur with increased MAL-1 activity and conditions associated with increased expression or activity of MAL-1. Enhancers of MAL-1 activity are useful for treating medical conditions, disease or disorder associated with a decrease in MAL-1 expression or activity and it is desirable to increase MAL-1 function. Such disease or medical conditions include increasing an immune response, e.g. use as a vaccine or vaccine adjuvant, increased response to bacterial and viral infection, as a therapeutic immunotherapies including anticancer immunotherapy treatments. Thus, therapeutics discovered by screening MAL-1 polypeptide fragments for agonistic or antagonistic activity have properties that make them suitable for use as: anti-inflammatory, keratolytic agent, anti-HIV therapeutic, anti-allergic, antianaemic, antiarteriosclerotic; antiasthmatic, antidiabetic, nephrotropic; cancer therapeutic, antigout; dermatological therapeutic; antithyroid; virucide; hepatotropic; immunosuppressive; cytostatic; fungicide; protozoacide; antibacterial, immunological disorder therapeutics; viral infection therapeutic, bacterial infection therapeutic; fungal infection therapeutic; and parasitic infection therapeutic.

Additional therapeutic uses of MAL-1 antagonists or agonists discovered according to the screening methods of this invention include immunological disorders (e.g. inflammation, actinic keratosis, AIDS, Addison's disease), haematopoietic cancer, infections caused by virus (e.g. adenovirus, parvovirus, coronavirus), bacteria (e.g. Staphylococcus, Streptococcus, Shigella), fungi (e.g. Aspergillus, Blastomyces), parasites (e.g. Plasmodium, Trypanosoma, intestinal protozoa), cell proliferative disorders (e.g. actinic keratosis, arteriosclerosis, bursitis), and cancers (e.g. leukemia, melanoma, sarcoma).

Accordingly, MAL-1 antagonists or agonists, depending upon whether decreased MAL-1 activity is desired or increased MAL-1 activity is desired, can be used to treat a number of indications, including graft versus host disease, asthma, allergies, transplant rejection, multiple sclerosis, rheumatoid arthritis, SLE, diabetes, including insulin resistant diabetes and juvenile diabetes, Alzheimer's Disease, inflammatory bowel disease, Crohn's Disease, anemia, pernicious anemia, atrophic gastritis, Wegener granulomatosis, discoid lupus erythematosus, ulcerative colitis, cold agglutinin-relating disease, Goodpasture's syndrome, primary biliary cirrhosis, sympathetic ophthalmitis, hyperthyroidism, Sjogren syndrome, hepatitis, including autoimmune hepatitis, autoimmune hemolytic anemia, myasthenia gravis, systemic scleroderma, systemic lupus erythematosus, polyleptic cold hemoglobinuria, polymyositis, periarteritis nodosa, Addison's disease, purpura hemorrhagica, Basedow's disease, leukopenia, Behcet's disease, climacterium praecox, rheumatopyra, chronic thyroiditis, Hodgkin's disease, HIV-infections, atopic dermatitis, allergic nasitis, pollinosis, adult respiratory distress syndrome, ankylosing spondylitis, arteriosclerosis, atherosclerosis, contact dermatitis, autoimmune polyendocrinopathy-candidiasis-ectodermal dystrophy, bursitis, cholecystitis, cirrhosis, emphysema, acute coronary syndrome, heart failure, dermatomyositis, erythroblastosis fetalis, glomerulonephritis, mixed connective tissue diseases, myocardial or pericardial inflammation, pancreatitis, osteoarthritis, complications of cancer, hemodialysis, and extracorporeal circulation, trauma, and hematopoietic cancer including lymphoma, leukemia, myeloma and complications of infection caused by a bacterial agent classified as pneumococcus, staphylococcus, corynebactgerium, clostridium meningococcus, gonococcus, listeria, moraxella, legionella, bordetella, gram-negative enterobacterium including shigella, campylobacter, pseudomonas, bivrio, brucella, francisella, yersinia, bartonella, mycobacterium, spirochaetale, chlamydia, or mycoplasma and apitoxin-allergy. In addition, inhibitors of MAL-1 are efficacious in treatment and prevention of septic shock which results from production or administration of excessive IFN-.gamma. Thus, MAL-1 inhibitors find a variety of uses as anti-autoimmune-diseases, anti-allergies, anti-inflammatories, immunosuppressants, hematopoietics, leukopoietics, thrombopoietics, analgesics and antipyretics directed to treatment and/or prevention of susceptive diseases as illustrated in the above.

In addition to LPS, TLR-4 recognizes a cellular fibronectin that is produced in response to tissue injury. Okamura et al. J Biol. Chem. 273, 10229–10233, 2001. The response to TLR-4 recognition includes the induction of genes encoding proinflammatory cytokines and matrix metalloproteinases. Thus, antagonists of MAL-1 activity are useful for antagonizing negative effects of tissue injury, including injuries involving heat shock protein. Agonists of MAL-1 may be used to treat tissue injury when an individual's response to tissue injury is not sufficient for healing.

Compositions of the present invention may contain a polypeptide or MAL-1 antagonist or agonist in any form described herein, such as native proteins, variants, derivatives, oligomers, and biologically active fragments. In particular embodiments, the composition comprises a soluble polypeptide, a small molecule, an antibody or an oligomer comprising soluble MAL-1 polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCI, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury (for example, intracoronary or intra tumor administration or injection into a joint undergoing an inflammatory reaction). Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Moreover, it has been found that DNA encoding a polypeptide can be administered to a mammal in such a way that it is taken up by cells, and expressed. The resultant protein will then be available to exert a therapeutic effect. Accordingly, compositions comprising nucleic acids in physiologically acceptable formulations are also contemplated. DNA may be formulated for injection, for example.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide or a DNA encoding a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (Proc. Natl. Acad. Sci. USA 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')2 fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

The following examples are provided to further illustrate particular embodiments of the invention, and are not to be construed as limiting the scope of the present invention.

EXAMPLE 1

This example describes the identification and isolation of a homolog of the IL-1 signaling adaptor molecule MyD88. High throughput sequencing of ESTs isolated from human dendritic cells revealed a clone exhibiting some degree of similarity to the cytoplasmic domain of members of the IL-1R/Toll family).

Appropriate primers were designed, and the novel DNA was cloned from a human dendritic cell cDNA library; the nucleotide and amino acid sequence of this protein, which was referred to as MyD88 Adaptor-Like protein 1 (MAL-1) are shown in SEQ ID NO:1 and 2.

Using the radiation hybrid technique, the cloned protein was mapped to chromosome 11q23–24.

EXAMPLE 2

This example describes the construction and expression of a recombinant Glutathione S-transferase (GST)/MAL-1 fusion protein. PCR primers are synthesized for use with a MAL-1 template, and PCR amplified product is obtained. An EcoR1 site is added to each end of the amplified product. This PCR product is ligated into the unique EcoR1 cloning site of the vector pGEX2T (Patent: EP 0293249-A 4 30 Nov. 1988; AMRAD CORPORATION LIMITED) such that the coding sequences of the glutathione S-transferase gene and MAL-1 are in the same frame. E. coli strain DH10B is transformed with the resultant vector and a one-liter culture is grown. Transcription of the GST/MAL-1 gene is induced by addition of IPTG (0.1 mM) to the bacterial culture for three hours. Bacterial cells are harvested and lysed according to methods well known in the art (see, for example, Smith D. B., Johnson K. S.; Single-step purification of polypeptides expressed in E. coli as fusions with glutathione S-transferase. Gene 67:31–40(1988)). The lysate containing solubilized GST/MAL-1 fusion protein is purified on 1 mL of Glutathione-Agarose beads (Pharmacia), according to the directions supplied by the manufacturer.

EXAMPLE 3

This example illustrates the preparation of monoclonal antibodies against MAL-1. Preparations of purified recombinant MAL-1, for example, or transfected cells expressing high levels of MAL-1, are employed to generate monoclonal antibodies against MAL-1 using conventional techniques, such as those disclosed in U.S. Pat. No. 4,411,993. DNA encoding MAL-1 can also be used as an immunogen, for example, as reviewed by Pardoll and Beckerleg in Immunity 3:165, 1995. Such antibodies are likely to be useful as components of diagnostic or research assays for MAL-1 or MAL-1 activity, or in affinity purification of MAL-1.

To immunize rodents, MAL-1 immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 µg subcutaneously into a selected rodent, for example, BALB/c mice or Lewis rats. DNA may be given intradermally (Raz et al., Proc. Natl. Acad. Sci. USA 91:9519, 1994) or intamuscularly (Wang et al., Proc. Natl. Acad. Sci. USA 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS 1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with MAL-1, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic rodents to produce ascites containing high concentrations (>1 mg/ml) of anti-MAL-1 monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to MAL-1 protein.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention. The relevant disclosures of references cited herein are specifically incorporated by reference.

EXAMPLE 4

The following describes studies which demonstrate that a polypeptide of the present invention activates NF-κB, Jun-N-terminal kinase (JNK) and the extracellular signal regulated kinases ERK1 and ERK2. Expression vectors containing from 1–80 ng of the MAL-1 polypeptide of SEQ ID NO:2 or the MyD88 polypeptide were transfected into HEK293 cells. The NF-κB assays utilized a reporter system that included a plasmid having 5 NF-κB sites upstream of luciferase. The Jun-N terminal kinase assays and ERK1 and ERK2 assays utilized a reporter system that included a plasmid encoding GAIA fused to c-Jun or Elkl along with a GAL4 luciferase reporter plasmid. Twenty-four hours after the expression vectors were transfected into the cells, NF-κB, JNK and ERK1 and ERK2 were measured by assaying for luciferase. The specificity of each assay was determined by adding a specific inhibitor for each signal. For NF-κB specificity, a I-κB superrepressor was co-transfected. For ERK1 and ERK2 specificity, the MEK1 inhibitor PD98059 was added and the JNK interacting protein JIP was co-transfected to check for JNK specificity. Immunoblot analysis demonstrated the expression of a MAL-1 polypeptide of this invention and MyD88 over the plasmid concentration range that was tested.

EXAMPLE 5

The following describes studies that demonstrate that a MAL-1 polypeptide of the present invention signals through MyD88.

HEK 293 cells were transfected with a 5×NF-κB reporter gene plasmid, and co-transfected with plasmids encoding a MAL-1 polypeptide of this invention or MyD88 and increasing concentrations of the isolated TIR domain from MyD88 (10, 50 and 80ng). Luciferase reporter gene activity was measured as described in Example 4.

In a yeast two hybrid assay, full length MAL-1 of SEQ ID NO:2 and MyD88 were sub-cloned into either pGBKT7 (Clontech) downstream of the GAL4 DNA binding domain, or into pACT2 (Clontech) downstream of the GAL4 activation domain. The presence of interacting pairs is indicated by transactivation of the His3 reporter gene in yeast which confers the ability to grow on media lacking histidine. The combinations were tested for either Leu-Trp- plate which indicated the presence of both plasmids or the His-Leu-Trp- plate which indicates protein-protein interactions.

HEK293 cells were transfected with full length labelled MyD88 (AU-1-MyD88) or full-length labelled MAL-1 (HA-MAL-1) or labelled TIR domain of MAL-1 (HA-TIR-MAL-1) or labelled TIR domain of MyD88 (AU-1-TIR-MyD88). After incubation lysates were prepared and incubated with an anti-AU1 antibody which immunoprecipitates the tagged MyD88. Tagged MAL-1 was detected in the immunoprecipitates by immunoblotting using an anti-HA antibody.

The results of the above described experiments showed that the stimulatory effects of MyD88 itself were inhibited by overexpression of its own isolated TIR domain. The yeast hybrid assays showed that MAL-1 and MyD88 are capable of homotypic and heterotypic association. Finally, the co-immunoprecipitations demonstrated that MAL-1 associates with MyD88. Extracts of cells transfected with epitope-tagged expression constructs of MAL-1 and MyD88 (full length and those containing only the TIR domains) complexes of both proteins were specifically immunoprecipitated.

EXAMPLE 6

The following describes studies which support the conclusion that MAL-1 does not signal through IRAK.

HEK 293 cells were transfected with a 5 × NF-κB reporter gene plasmid and co-transfected with plasmids encoding MAL-1 of SEQ ID NO:2 or MyD88 and increasing concentrations of IRAK. Luciferase reporter gene activity was measured. HEK293 cells were transfected with HA-MAL-1 and IRAK and the resulting overexpressed proteins were immunoprecipitated using an anti-HA antibody to isolate MAL-1 complexes and interactions were detected by western blotting to detect anti-IRAK. IRAK could not be detected in the anti-HA-MAL immunoprecipitates. HEK293 cells were transfected with AU-1-MyD88 and IRAK and the resulting overexpressed proteins were immunoprecipitated using an anti-AU1 antibody to isolate MyD88 complexes and interactions were detected by western blotting for anti-IRAK. IRAK was detected in the anti-Aul-MyD88 immunoprecipitates. These results indicate that MyD88 signals through IRAK, but MAL-1 does not.

EXAMPLE 7

The following experiments demonstrate that MAL-1 of this invention, like MyD88, signals through IRAK2.

HEK 293 cells were transfected with a 5×NF-κB reporter gene plasmid and co-transfected with plasmids encoding MAL-1 of SEQ ID NO:2 or MyD88 and increasing concentrations of K-IRAK-2. Following transfection luciferase reporter gene activity was measured.

Additionally, HEK293 cells were transfected with HA-MAL and myc-IRAK-2. Following transfection lysates were prepared and then incubated with an anti-HA antibody which immunoprecipitates tagged MAL-1. Tagged IRAK-2 was detected in the immunoprecipitates by immunoblotting using an anti-myc antibody. In a similar transfection experiment, HEK293 cells were transfected with HA-TIR-MAL-1 and myc-IRAK-2. Following transfection lysates were prepared and then incubated with an anti-HA antibody which immunoprecipitates the tagged TIR-MAL-1. Tagged IRAK-2 was detected in the anti-HA-TIR-MAL immunoprecipitates by immunoblotting using an anti-myc antibody. Finally, HEK293 cells were transfected with AU-1-MyD88 and myc-IRAK-2. Following transfection lysates were prepared and then incubated with an anti-AU-1 antibody which immunoprecipitates the tagged MyD88. Tagged IRAK-2 was detected in the anti-AU-1-MyD88 immunoprecipitates by immunoblotting using an anti-myc antibody.

Dominant negative IRAK2 blocked the effect of MAL-1 and MyD88 and the co-precipitation experiments showed the MAL-1 can not interact with IRAK. MyD88, however, was co-immunoprecipitated with IRAK. Overall, the results of these immunoprecipitation and immunoblotting experiments confirm that IRAK2 is required for MAL-1 signalling which contrasts with the results from Example 6 which show that IRAK is not required.

EXAMPLE 8

The following studies demonstrate a role for TRAF-6 and TAK-1 in MAL-1 signalling. HEK 293 cells were transfected with an 5×NF-κB reporter gene plasmid and co-transfected with plasmids encoding MAL or MyD88 and increasing concentrations of TRAF-6 dominant negative or TAK-1 dominant negative. Luciferase reporter gene activity measured by standard methods.

Dominant negative forms of both TRAF-6 and the protein kinase TAK-1 inhibited NF-κB activation by MAL-1 or MyD88, in a dose-dependent manner. This demonstrates a role for TRAF6 and TAK-1 in the MAL-1 and MyD88 signaling pathways

EXAMPLE 9

The following studies demonstrate that MAL-1 is required for TLR-4 and LPS signalling.

HEK 293 cells were transfected with a 5 x NF-κB reporter gene plasmid and co-transfected with plasmids encoding empty vector, TLR-4 or IL-1RacP. The cells were also co-transfected with the isolated TIR domains from MAL-1 or MyD88. Luciferase reporter gene activity was measured.

The human macrophage cell line THP-1 (ATCC, Manassas, Va.) were transfected with a 5×NF-κB reporter and increasing amounts of plasmid encoding the isolated TIR domain of MAL for 24 hours. The cells were left untreated or incubated with LPS from E. coli Serotype 026:B6 (Sigma) for 6 hours and the luciferase activity measured.

The effect of isolating the TIR domain from MAL-1 which, by analogy with MyD88, should act as a dominant inhibitor showed that increasing concentrations of the isolated TIR domain from MAL-1 activated NF-κB. This response however was never as strong as that observed with full length MAL.

Over-expression of the isolated TIR domain from MyD88 had no effect. Over-expression of TLR-4 in HEK293 cells activates NF-κB. Importantly, co-expression with the isolated TIR domain from MAL-1 reduced this signal to the level of this domain alone. The effect was specific for TLR-4, as the response in cells transfected with the IL-1 receptor accessory protein (or both the Type I IL-1 receptor and the IL-1 receptor accessory protein) was not inhibited, although this stimulus was inhibited by the isolated TIR domain from MyD88. Finally, transfection of the isolated TIR domain from MAL-1 into the macrophage cell line THP-1, blocked the activation of NF-κB by LPS.

These results demonstrate that MAL-1 acts as an adapter for TLR-4 signalling.

---

What is claimed is:

1. A polynucleotide consisting of a nucleic acid that encodes a fragment of the polypeptide consisting of SEQ ID NO:2, wherein the fragment activates NFκB.

2. A polynucleotide consisting of a nucleic acid encoding a polypeptide that is at least 80% identical to a polypeptide of claim 1, wherein the polypeptide activates NFκB.

3. A polynucleotide consisting of a nucleic acid encoding a polypeptide consisting of polypeptides selected from the group consisting of:

a) amino acids 68–236 of SEQ ID NO:2;
b) amino acids 86–236 of SEQ ID NO:2;
c) amino acids 86–217 of SEQ ID NO:2; and,
d) amino acids 68–217 of SEQ ID NO:2.
e) amino acids x–236 of SEQ ID NO:2 where x is any of amino acids 68–86 of SEQ IDNO:2;
f) amino acid x1–217 of SEQ ID NO:2, where x1 is any of amino acids 68–86 of SEQ ID NO:2.

4. A polynucleotide that encodes the polypeptide of SEQ ID NO:2 with the proviso that the Pro at amino acid 125 is His.

5. An expression vector comprising a polynucleotide of claim 1.

6. An expression vector comprising a polynucleotide of claim 3.

7. A host cell transformed or transfected with the expression vector of claim 1.

8. A host cell transformed or transfected with the expression vector of claim 3.

9. A method for preparing a polypeptide, the method comprising culturing the host cell of claim 7 under conditions suitable for expressing the polypeptide.

* * * * *

SEQUENCE LISTING

```
<160> NUMBER OF SEQ ID NOS: 2

<210> SEQ ID NO 1
<211> LENGTH: 977
<212> TYPE: DNA
<213> ORGANISM: Homo sapiens
<220> FEATURE:
<221> NAME/KEY: CDS
<222> LOCATION: (162)..(869)

<400> SEQUENCE: 1
tcttggaacg agacgacctg ctgcccgcgc agtccgcgca gccctcatcg caactgggcc      60
cgcgcgcagg atggctgctt catgaggtca agactgggtc tcctccctcc tcccccttca     120
ccaatgcctg gtctcacggg gctagttttg accccacgc t atg gca tca tcg acc     176
                                           Met Ala Ser Ser Thr
                                             1               5 tcc ctc cca gct cct ggc tct cgg cct aag aag cct cta ggc aag atg      224
Ser Leu Pro Ala Pro Gly Ser Arg Pro Lys Lys Pro Leu Gly Lys Met
         10                  15                  20 gct gac tgg ttc agg cag acc ctg ctg aag aag ccc aag aag agg ccc      272
Ala Asp Trp Phe Arg Gln Thr Leu Leu Lys Lys Pro Lys Lys Arg Pro
```

```
                25                  30                  35
aac tcc cca gaa agc acc tcc agc gat gct tca cag cct acc tca cag         320
Asn Ser Pro Glu Ser Thr Ser Ser Asp Ala Ser Gln Pro Thr Ser Gln
         40                  45                  50 gac aac cca cta ccc cca agc ctc agc tca gtc acg tct ccc agc ctg         368
Asp Asn Pro Leu Pro Pro Ser Leu Ser Ser Val Thr Ser Pro Ser Leu
 55                  60                  65 cca ccc aca cat gcg agt gac agt ggc agt agt cgc tgg agc aaa gac         416
Pro Pro Thr His Ala Ser Asp Ser Gly Ser Ser Arg Trp Ser Lys Asp
 70                  75                  80                  85 tat gac gtc tgc gtg tgc cac agt gag gaa gac ctg gtg gcc gcc cag         464
Tyr Asp Val Cys Val Cys His Ser Glu Glu Asp Leu Val Ala Ala Gln
                 90                  95                 100 gac ctg gtc tcc tac ttg gaa ggc agc act gcc agc ctg cgc tgc ttc         512
Asp Leu Val Ser Tyr Leu Glu Gly Ser Thr Ala Ser Leu Arg Cys Phe
                105                 110                 115 ctg caa ctc cgg gat gca acc cca ggc ggc gct ata gtg tcc gag ctg         560
Leu Gln Leu Arg Asp Ala Thr Pro Gly Gly Ala Ile Val Ser Glu Leu
        120                 125                 130 tgc cag gca ctg agc agt agt cac tgc cgg gtg ctg ctc atc acg ccg         608
Cys Gln Ala Leu Ser Ser Ser His Cys Arg Val Leu Leu Ile Thr Pro
    135                 140                 145 ggc ttc ctt cag gac ccc tgg tgc aag tac cag atg ctg cag gcc ctg         656
Gly Phe Leu Gln Asp Pro Trp Cys Lys Tyr Gln Met Leu Gln Ala Leu
150                 155                 160                 165 acc gag gct cca ggg gcc gag ggc tgc acc atc ccc ctg ctg tcg ggc         704
Thr Glu Ala Pro Gly Ala Glu Gly Cys Thr Ile Pro Leu Leu Ser Gly
                170                 175                 180 ctc agc aga gct gcc tac cca cct gag ctc cga ttc atg tac tac gtc         752
Leu Ser Arg Ala Ala Tyr Pro Pro Glu Leu Arg Phe Met Tyr Tyr Val
            185                 190                 195 gat ggc agg ggc cct gat ggt ggc ttt cgt caa gtc aaa gaa gct gtc         800
Asp Gly Arg Gly Pro Asp Gly Gly Phe Arg Gln Val Lys Glu Ala Val
        200                 205                 210 atg cgt tgt aag cta cta cag gag gga gaa ggg gaa cgg gat tca gct         848
Met Arg Cys Lys Leu Leu Gln Glu Gly Glu Gly Glu Arg Asp Ser Ala
    215                 220                 225 aca gta tct gat cta ctt tga cttttaggag acagccctgt agcctagtag           899
Thr Val Ser Asp Leu Leu
230                 235 ttcaaagcgc agcttctgga aaggctgtc ggggtttgta tcctggctcc tgcagcaggt        959
cgtctcgttc caagatcc                                                    977

<210> SEQ ID NO 2
<211> LENGTH: 235
<212> TYPE: PRT
<213> ORGANISM: Homo sapiens

<400> SEQUENCE: 2

Met Ala Ser Ser Thr Ser Leu Pro Ala Pro Gly Ser Arg Pro Lys Lys
1               5                   10                  15

Pro Leu Gly Lys Met Ala Asp Trp Phe Arg Gln Thr Leu Leu Lys Lys
            20                  25                  30

Pro Lys Lys Arg Pro Asn Ser Pro Glu Ser Thr Ser Ser Asp Ala Ser
        35                  40                  45

Gln Pro Thr Ser Gln Asp Asn Pro Leu Pro Ser Leu Ser Ser Val
    50                  55                  60

Thr Ser Pro Ser Leu Pro Pro Thr His Ala Ser Asp Ser Gly Ser Ser
```

-continued

```
65                  70                  75                  80
Arg Trp Ser Lys Asp Tyr Asp Val Cys Val Cys His Ser Glu Glu Asp
                85                  90                  95

Leu Val Ala Ala Gln Asp Leu Val Ser Tyr Leu Glu Gly Ser Thr Ala
            100                 105                 110

Ser Leu Arg Cys Phe Leu Gln Leu Arg Asp Ala Thr Pro Gly Gly Ala
            115                 120                 125

Ile Val Ser Glu Leu Cys Gln Ala Leu Ser Ser Ser His Cys Arg Val
            130                 135                 140

Leu Leu Ile Thr Pro Gly Phe Leu Gln Asp Pro Trp Cys Lys Tyr Gln
145                 150                 155                 160

Met Leu Gln Ala Leu Thr Glu Ala Pro Gly Ala Glu Gly Cys Thr Ile
            165                 170                 175

Pro Leu Leu Ser Gly Leu Ser Arg Ala Ala Tyr Pro Pro Glu Leu Arg
            180                 185                 190

Phe Met Tyr Tyr Val Asp Gly Arg Gly Pro Asp Gly Gly Phe Arg Gln
            195                 200                 205

Val Lys Glu Ala Val Met Arg Cys Lys Leu Leu Gln Glu Gly Glu Gly
    210                 215                 220

Glu Arg Asp Ser Ala Thr Val Ser Asp Leu Leu
225                 230                 235
```